(12) United States Patent
Ghose

(10) Patent No.: US 12,189,449 B2
(45) Date of Patent: *Jan. 7, 2025

(54) ENERGY AWARE PROCESSING LOAD DISTRIBUTION SYSTEM AND METHOD

(71) Applicant: The Research Foundation for The State University of New York, Binghamton, NY (US)

(72) Inventor: Kanad Ghose, Vesta, NY (US)

(73) Assignee: The Research Foundation for The State University of New York, Binghamton, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/387,052

(22) Filed: Nov. 5, 2023

(65) Prior Publication Data

US 2024/0069617 A1 Feb. 29, 2024

Related U.S. Application Data

(60) Continuation of application No. 17/543,122, filed on Dec. 6, 2021, now Pat. No. 11,809,254, which is a
(Continued)

(51) Int. Cl.
*G06F 1/3209* (2019.01)
*A61K 36/185* (2006.01)
(Continued)

(52) U.S. Cl.
CPC .......... *G06F 1/3209* (2013.01); *A61K 36/185* (2013.01); *B03B 1/00* (2013.01);
(Continued)

(58) Field of Classification Search
CPC ....... G06F 1/3209; G06F 1/20; A61K 36/185; B03B 1/00
See application file for complete search history.

(56) References Cited

U.S. PATENT DOCUMENTS 3,339,410 A 9/1967 Steru
3,391,411 A 7/1968 Miller, Jr.
(Continued)

OTHER PUBLICATIONS

U.S. Appl. No. 10/209,580, filed Feb. 19, 2019, Son et al.

*Primary Examiner* — Matthew Mikels
(74) *Attorney, Agent, or Firm* — Hoffberg & Associates; Steven M. Hoffberg

(57) ABSTRACT

A method for controlling a data center, comprising a plurality of server systems, each associated with a cooling system and a thermal constraint, comprising: a concurrent physical condition of a first server system; predicting a future physical condition based on a set of future states of the first server system; dynamically controlling the cooling system in response to at least the input and the predicted future physical condition, to selectively cool the first server system sufficient to meet the predetermined thermal constraint; and controlling an allocation of tasks between the plurality of server systems to selectively load the first server system within the predetermined thermal constraint and selectively idle a second server system, wherein the idle second server system can be recruited to accept tasks when allocated to it, and wherein the cooling system associated with the idle second server system is selectively operated in a low power consumption state.

20 Claims, 2 Drawing Sheets

Integrated control strategy for servers and cooling system

Related U.S. Application Data division of application No. 15/694,459, filed on Sep. 1, 2017, now Pat. No. 10,095,969, which is a continuation of application No. 14/153,540, filed on Jan. 13, 2014, now Pat. No. 9,753,465, which is a continuation of application No. 12/841,169, filed on Jul. 21, 2010, now Pat. No. 8,631,411.

(60) Provisional application No. 61/227,361, filed on Jul. 21, 2009.

(51) Int. Cl.
| | | |
|---|---|---|
| *B03B 1/00* | (2006.01) | |
| *B03B 5/02* | (2006.01) | |
| *B03B 5/58* | (2006.01) | |
| *B03B 11/00* | (2006.01) | |
| *G05D 23/19* | (2006.01) | |
| *G06F 1/20* | (2006.01) | |
| *G06F 1/3203* | (2019.01) | |
| *G06F 1/3206* | (2019.01) | |
| *G06F 1/3228* | (2019.01) | |
| *G06F 9/455* | (2018.01) | |
| *G06F 9/48* | (2006.01) | |
| *G06F 9/50* | (2006.01) | |
| *G06F 13/40* | (2006.01) | |
| *G06K 19/07* | (2006.01) | |
| *G06K 19/077* | (2006.01) | |
| *H04L 9/40* | (2022.01) | |
| *H04L 69/329* | (2022.01) | |
| *H05K 7/20* | (2006.01) | |

(52) U.S. Cl.
CPC ............... *B03B 5/02* (2013.01); *B03B 5/58* (2013.01); *B03B 11/00* (2013.01); *G05D 23/19* (2013.01); *G06F 1/20* (2013.01); *G06F 1/206* (2013.01); *G06F 1/3203* (2013.01); *G06F 1/3206* (2013.01); *G06F 1/3228* (2013.01); *G06F 9/45558* (2013.01); *G06F 9/4893* (2013.01); *G06F 9/5094* (2013.01); *G06F 13/409* (2013.01); *G06K 19/0723* (2013.01); *G06K 19/07705* (2013.01); *G06K 19/07722* (2013.01); *H04L 9/40* (2022.05); *H04L 69/329* (2013.01); *H05K 7/20836* (2013.01); *G06F 2009/4557* (2013.01); *Y02D 10/00* (2018.01)

(56) References Cited

U.S. PATENT DOCUMENTS

| | | |
|---|---|---|
| 4,823,290 A | 4/1989 | Fasack et al. |
| 4,962,734 A | 10/1990 | Jorgensen |
| 5,095,712 A | 3/1992 | Narreau |
| 5,216,623 A | 6/1993 | Barrett et al. |
| 5,367,670 A | 11/1994 | Ward et al. |
| 5,410,448 A | 4/1995 | Barker, III et al. |
| 5,462,225 A | 10/1995 | Massara et al. |
| 5,581,478 A | 12/1996 | Cruse et al. |
| 5,657,641 A | 8/1997 | Cunningham et al. |
| 5,682,949 A | 11/1997 | Ratcliffe et al. |
| 5,718,628 A | 2/1998 | Nakazato et al. |
| 5,735,134 A | 4/1998 | Liu et al. |
| 5,850,539 A | 12/1998 | Cook et al. |
| 5,995,729 A | 11/1999 | Hirosawa et al. |
| 6,055,480 A | 4/2000 | Nevo et al. |
| 6,078,943 A | 6/2000 | Yu |
| 6,117,180 A | 9/2000 | Dave et al. |
| 6,134,511 A | 10/2000 | Subbarao |
| 6,179,489 B1 | 1/2001 | So et al. |
| 6,189,106 B1 | 2/2001 | Anderson |
| 6,216,956 B1 | 4/2001 | Ehlers et al. |
| 6,223,274 B1 | 4/2001 | Catthoor et al. |
| 6,246,969 B1 | 6/2001 | Sinclair et al. |
| 6,289,267 B1 | 9/2001 | Alexander et al. |
| 6,289,488 B1 | 9/2001 | Dave et al. |
| 6,298,370 B1 | 10/2001 | Tang et al. |
| 6,341,347 B1 | 1/2002 | Joy et al. |
| 6,347,627 B1 | 2/2002 | Frankie et al. |
| 6,351,808 B1 | 2/2002 | Joy et al. |
| 6,374,627 B1 | 4/2002 | Schumacher et al. |
| 6,494,050 B2 | 12/2002 | Spinazzola et al. |
| 6,507,862 B1 | 1/2003 | Joy et al. |
| 6,542,991 B1 | 4/2003 | Joy et al. |
| 6,574,104 B2 | 6/2003 | Patel et al. |
| 6,672,955 B2 | 1/2004 | Charron |
| 6,694,347 B2 | 2/2004 | Joy et al. |
| 6,694,759 B1 | 2/2004 | Bash et al. |
| 6,714,977 B1 | 3/2004 | Fowler et al. |
| 6,718,277 B2 | 4/2004 | Sharma |
| 6,721,672 B2 | 4/2004 | Spitaels et al. |
| 6,735,630 B1 | 5/2004 | Gelvin et al. |
| 6,745,579 B2 | 6/2004 | Spinazzola et al. |
| 6,804,616 B2 | 10/2004 | Bodas |
| 6,819,563 B1 | 11/2004 | Chu et al. |
| 6,826,607 B1 | 11/2004 | Gelvin et al. |
| 6,827,142 B2 | 12/2004 | Winkler et al. |
| 6,832,251 B1 | 12/2004 | Gelvin et al. |
| 6,853,097 B2 | 2/2005 | Matsuda et al. |
| 6,859,366 B2 | 2/2005 | Fink |
| 6,859,831 B1 | 2/2005 | Gelvin et al. |
| 6,862,179 B2 | 3/2005 | Beitelmal et al. |
| 6,885,920 B2 | 4/2005 | Yakes et al. |
| 6,964,539 B2 | 11/2005 | Bradley et al. |
| 6,967,283 B2 | 11/2005 | Rasmussen et al. |
| 7,020,586 B2 | 3/2006 | Snevely |
| 7,020,701 B1 | 3/2006 | Gelvin et al. |
| 7,031,870 B2 | 4/2006 | Sharma et al. |
| 7,051,946 B2 | 5/2006 | Bash et al. |
| 7,062,304 B2 | 6/2006 | Chauvel et al. |
| 7,085,133 B2 | 8/2006 | Hall |
| 7,089,443 B2 | 8/2006 | Albonesi et al. |
| 7,139,999 B2 | 11/2006 | Bowman-Amuah |
| 7,148,796 B2 | 12/2006 | Joy et al. |
| 7,155,318 B2 | 12/2006 | Sharma et al. |
| 7,155,617 B2 | 12/2006 | Gary et al. |
| 7,174,194 B2 | 2/2007 | Chauvel et al. |
| 7,174,468 B2 | 2/2007 | Gary et al. |
| 7,184,866 B2 | 2/2007 | Squires et al. |
| 7,197,433 B2 | 3/2007 | Patel et al. |
| 7,219,067 B1 | 5/2007 | Mcmullen et al. |
| 7,219,249 B1 | 5/2007 | Ghose et al. |
| 7,228,441 B2 | 6/2007 | Fung |
| 7,251,547 B2 | 7/2007 | Bash et al. |
| 7,251,709 B2 | 7/2007 | Williams |
| 7,313,503 B2 | 12/2007 | Nakagawa et al. |
| 7,315,448 B1 | 1/2008 | Bash et al. |
| 7,316,021 B2 | 1/2008 | Joy et al. |
| 7,330,983 B2 | 2/2008 | Chaparro et al. |
| 7,365,973 B2 | 4/2008 | Rasmussen et al. |
| 7,366,632 B2 | 4/2008 | Hamann et al. |
| 7,378,165 B2 | 5/2008 | Brignone et al. |
| 7,401,333 B2 | 7/2008 | Vandeweerd |
| 7,403,391 B2 | 7/2008 | Germagian et al. |
| 7,421,601 B2 | 9/2008 | Bose et al. |
| 7,426,453 B2 | 9/2008 | Patel et al. |
| 7,472,043 B1 | 12/2008 | Low et al. |
| 7,500,001 B2 | 3/2009 | Tameshige et al. |
| 7,549,069 B2 | 6/2009 | Ishihara et al. |
| 7,558,649 B1 | 7/2009 | Sharma et al. |
| 7,562,243 B1 | 7/2009 | Ghose |
| 7,568,360 B1 | 8/2009 | Bash et al. |
| 7,584,475 B1 | 9/2009 | Lightstone et al. |
| 7,590,589 B2 | 9/2009 | Hoffberg |
| 7,596,476 B2 | 9/2009 | Rasmussen et al. |
| 7,620,480 B2 | 11/2009 | Patel et al. |
| 7,644,148 B2 | 1/2010 | Ranganathan et al. |
| 7,657,766 B2 | 2/2010 | Gonzalez et al. |
| 7,676,280 B1 | 3/2010 | Bash et al. |
| 7,685,601 B2 | 3/2010 | Iwamoto |
| 7,702,660 B2 | 4/2010 | Chan et al. |
| 7,726,144 B2 | 6/2010 | Larson et al. |

(56) References Cited

U.S. PATENT DOCUMENTS

| | | |
|---|---|---|
| 7,739,537 B2 | 6/2010 | Albonesi et al. |
| 7,757,103 B2 | 7/2010 | Savransky et al. |
| 7,797,367 B1 | 9/2010 | Gelvin et al. |
| 7,799,474 B2 | 9/2010 | Lyon et al. |
| 7,818,507 B2 | 10/2010 | Yamazaki et al. |
| 7,844,440 B2 | 11/2010 | Nasle et al. |
| 7,844,687 B1 | 11/2010 | Gelvin et al. |
| 7,881,910 B2 | 2/2011 | Rasmussen et al. |
| 7,885,795 B2 | 2/2011 | Rasmussen et al. |
| 7,904,905 B2 | 3/2011 | Cervini |
| 7,908,126 B2 | 3/2011 | Bahel et al. |
| 7,912,955 B1 | 3/2011 | Machiraju et al. |
| 7,975,156 B2 | 7/2011 | Artman et al. |
| 7,979,250 B2 | 7/2011 | Archibald et al. |
| 7,992,151 B2 | 8/2011 | Warrier et al. |
| 8,006,111 B1 | 8/2011 | Faibish et al. |
| 8,015,567 B2 | 9/2011 | Hass |
| 8,020,163 B2 | 9/2011 | Nollet et al. |
| 8,051,310 B2 | 11/2011 | He et al. |
| 8,099,731 B2 | 1/2012 | Li et al. |
| 8,117,367 B2 | 2/2012 | Conti et al. |
| 8,135,851 B2 | 3/2012 | Pilkington et al. |
| 8,140,658 B1 | 3/2012 | Gelvin et al. |
| 8,155,922 B2 | 4/2012 | Loucks |
| 8,200,995 B2 | 6/2012 | Shiga et al. |
| 8,219,362 B2 | 7/2012 | Shrivastava et al. |
| 8,219,993 B2 | 7/2012 | Johnson et al. |
| 8,228,046 B2 | 7/2012 | Ingemi et al. |
| 8,244,502 B2 | 8/2012 | Hamann et al. |
| 8,245,059 B2 | 8/2012 | Jackson |
| 8,249,825 B2 | 8/2012 | Vangilder et al. |
| 8,260,628 B2 | 9/2012 | Lopez et al. |
| 8,271,807 B2 | 9/2012 | Jackson |
| 8,271,813 B2 | 9/2012 | Jackson |
| 8,276,008 B2 | 9/2012 | Jackson |
| 8,301,315 B2 | 10/2012 | Dawson et al. |
| 8,302,098 B2 | 10/2012 | Johnson et al. |
| 8,321,712 B2 | 11/2012 | Ghose |
| 8,327,158 B2 | 12/2012 | Titiano et al. |
| 8,344,546 B2 | 1/2013 | Sarti |
| 8,365,176 B2 | 1/2013 | Campbell et al. |
| 8,397,088 B1 | 3/2013 | Ghose |
| 8,417,391 B1 | 4/2013 | Rombouts et al. |
| 8,424,006 B2 | 4/2013 | Jacobson et al. |
| 8,425,287 B2 | 4/2013 | Wexler |
| 8,438,364 B2 | 5/2013 | Venkataramani |
| 8,447,993 B2 | 5/2013 | Greene et al. |
| 8,452,999 B2 | 5/2013 | Barth et al. |
| 8,467,906 B2 | 6/2013 | Michael et al. |
| 8,473,265 B2 | 6/2013 | Hlasny et al. |
| 8,499,302 B2 | 7/2013 | Hass |
| 8,509,959 B2 | 8/2013 | Zhang et al. |
| 8,527,747 B2 | 9/2013 | Hintermeister et al. |
| 8,527,997 B2 | 9/2013 | Bell, Jr. et al. |
| 8,533,719 B2 | 9/2013 | Fedorova et al. |
| 8,549,333 B2 | 10/2013 | Jackson |
| 8,554,515 B2 | 10/2013 | Vangilder et al. |
| 8,560,677 B2 | 10/2013 | Vangilder et al. |
| 8,565,931 B2 | 10/2013 | Marwah et al. |
| 8,566,447 B2 | 10/2013 | Cohen et al. |
| 8,583,945 B2 | 11/2013 | Tran |
| 8,589,931 B2 | 11/2013 | Barsness et al. |
| 8,589,932 B2 | 11/2013 | Bower, III et al. |
| 8,595,586 B2 | 11/2013 | Borthakur et al. |
| 8,600,576 B2 | 12/2013 | Dawson et al. |
| 8,600,830 B2 | 12/2013 | Hoffberg |
| 8,612,688 B2 | 12/2013 | Venkataramani et al. |
| 8,612,785 B2 | 12/2013 | Brown et al. |
| 8,612,984 B2 | 12/2013 | Bell, Jr. et al. |
| 8,631,411 B1 | 1/2014 | Ghose |
| 8,639,113 B2 | 1/2014 | Decusatis et al. |
| 8,639,482 B2 | 1/2014 | Rasmussen et al. |
| 8,667,063 B2 | 3/2014 | Graham et al. |
| 8,677,365 B2 | 3/2014 | Bash et al. |
| 8,684,802 B1 | 4/2014 | Gross et al. |
| 8,688,413 B2 | 4/2014 | Healey et al. |
| 8,689,220 B2 | 4/2014 | Prabhakar et al. |
| 8,723,362 B2 | 5/2014 | Park et al. |
| 8,725,307 B2 | 5/2014 | Healey et al. |
| 8,736,109 B2 | 5/2014 | Park |
| 8,751,897 B2 | 6/2014 | Borthakur et al. |
| 8,776,069 B2 | 7/2014 | Prabhakar et al. |
| 8,793,328 B2 | 7/2014 | Lindamood et al. |
| 8,793,351 B2 | 7/2014 | Renzin |
| 8,798,964 B2 | 8/2014 | Rosenthal et al. |
| 8,820,113 B2 | 9/2014 | Heydari et al. |
| 8,825,219 B2 | 9/2014 | Gheerardyn et al. |
| 8,825,451 B2 | 9/2014 | Vangilder et al. |
| 8,832,111 B2 | 9/2014 | Venkataramani et al. |
| 8,838,281 B2 | 9/2014 | Rombouts et al. |
| 8,842,432 B2 | 9/2014 | Ehlen |
| 8,862,668 B2 | 10/2014 | Graham et al. |
| 8,867,213 B2 | 10/2014 | Furuta et al. |
| 8,869,158 B2 | 10/2014 | Prabhakar et al. |
| 8,874,836 B1 | 10/2014 | Hayes et al. |
| 8,885,335 B2 | 11/2014 | Magarelli |
| 8,897,017 B2 | 11/2014 | Brashers et al. |
| 8,903,876 B2 | 12/2014 | Michael et al. |
| 8,904,394 B2 | 12/2014 | Dawson et al. |
| 8,913,377 B2 | 12/2014 | Furuta |
| 8,914,155 B1 | 12/2014 | Shah et al. |
| 8,925,339 B2 | 1/2015 | Kearney et al. |
| 8,937,405 B2 | 1/2015 | Park |
| 8,949,081 B2 | 2/2015 | Healey |
| 8,949,632 B2 | 2/2015 | Kobayashi et al. |
| 8,954,675 B2 | 2/2015 | Venkataramani et al. |
| 8,972,217 B2 | 3/2015 | Vangilder et al. |
| 8,972,570 B1 | 3/2015 | Moreels et al. |
| 8,991,198 B2 | 3/2015 | Kearney et al. |
| 8,996,180 B2 | 3/2015 | Vangilder et al. |
| 8,996,810 B2 | 3/2015 | Liang |
| 9,015,324 B2 | 4/2015 | Jackson |
| 9,026,807 B2 | 5/2015 | Jackson |
| 9,027,024 B2 | 5/2015 | Mick et al. |
| 9,060,449 B2 | 6/2015 | Ehlen |
| 9,086,883 B2 | 7/2015 | Thomson et al. |
| 9,098,351 B2 | 8/2015 | Bell, Jr. et al. |
| 9,098,876 B2 | 8/2015 | Steven et al. |
| 9,104,493 B2 | 8/2015 | Molkov et al. |
| 9,122,525 B2 | 9/2015 | Barsness et al. |
| 9,122,717 B2 | 9/2015 | Liang |
| 9,135,063 B1 | 9/2015 | Ghose |
| 9,141,155 B2 | 9/2015 | Wiley |
| 9,144,181 B2 | 9/2015 | Wiley |
| 9,148,068 B2 | 9/2015 | Sarti |
| 9,159,042 B2 | 10/2015 | Steven et al. |
| 9,159,108 B2 | 10/2015 | Steven et al. |
| 9,164,566 B2 | 10/2015 | Ghose |
| 9,171,276 B2 | 10/2015 | Steven et al. |
| 9,173,327 B2 | 10/2015 | Wiley |
| 9,177,072 B2 | 11/2015 | Krishnamurthy et al. |
| 9,178,958 B2 | 11/2015 | Lindamood et al. |
| 9,192,077 B2 | 11/2015 | Iqbal |
| 9,208,207 B2 | 12/2015 | Venkataramani et al. |
| 9,219,644 B2 | 12/2015 | Renzin |
| 9,219,657 B2 | 12/2015 | Dawson et al. |
| 9,223,905 B2 | 12/2015 | Dalgas et al. |
| 9,235,441 B2 | 1/2016 | Brech et al. |
| 9,240,025 B1 | 1/2016 | Ward, Jr. et al. |
| 9,250,962 B2 | 2/2016 | Brech et al. |
| 9,264,466 B2 | 2/2016 | Graham et al. |
| 9,274,710 B1 | 3/2016 | Oikarinen et al. |
| 9,277,026 B2 | 3/2016 | Liang et al. |
| 9,286,642 B2 | 3/2016 | Hochberg et al. |
| 9,310,786 B2 | 4/2016 | Imhof et al. |
| 9,322,169 B2 | 4/2016 | Magarelli et al. |
| 9,335,747 B2 | 5/2016 | Steven et al. |
| 9,338,928 B2 | 5/2016 | Lehman |
| 9,342,376 B2 | 5/2016 | Jain et al. |
| 9,342,464 B2 | 5/2016 | Krishnamurthy et al. |
| 9,344,151 B2 | 5/2016 | Cenizal et al. |
| 9,354,683 B2 | 5/2016 | Patiejunas et al. |
| 9,355,060 B1 | 5/2016 | Barber et al. |
| 9,367,052 B2 | 6/2016 | Steven et al. |

(56) References Cited

U.S. PATENT DOCUMENTS

| | | |
|---|---|---|
| 9,367,825 B2 | 6/2016 | Steven et al. |
| 9,374,309 B2 | 6/2016 | Shaw et al. |
| 9,377,837 B2 | 6/2016 | Ghose |
| 9,753,465 B1 | 9/2017 | Ghose |
| 11,809,254 B2 * | 11/2023 | Ghose .................. A61K 36/185 |
| 2001/0042616 A1 | 11/2001 | Baer |
| 2002/0043969 A1 | 4/2002 | Duncan et al. |
| 2002/0059804 A1 | 5/2002 | Spinazzola et al. |
| 2002/0071031 A1 | 6/2002 | Lord et al. |
| 2002/0072868 A1 | 6/2002 | Bartone et al. |
| 2002/0078122 A1 | 6/2002 | Joy et al. |
| 2002/0149911 A1 | 10/2002 | Bishop et al. |
| 2003/0061258 A1 | 3/2003 | Rodgers et al. |
| 2003/0097478 A1 | 5/2003 | King |
| 2003/0115000 A1 | 6/2003 | Bodas |
| 2003/0115024 A1 | 6/2003 | Snevely |
| 2003/0147216 A1 | 8/2003 | Patel et al. |
| 2003/0158718 A1 | 8/2003 | Nakagawa et al. |
| 2003/0177406 A1 | 9/2003 | Bradley et al. |
| 2003/0232598 A1 | 12/2003 | Aljadeff et al. |
| 2004/0006584 A1 | 1/2004 | Vandeweerd |
| 2004/0020224 A1 | 2/2004 | Bash et al. |
| 2004/0065097 A1 | 4/2004 | Bash et al. |
| 2004/0065104 A1 | 4/2004 | Bash et al. |
| 2004/0073324 A1 | 4/2004 | Pierro et al. |
| 2004/0075984 A1 | 4/2004 | Bash et al. |
| 2004/0089009 A1 | 5/2004 | Bash et al. |
| 2004/0089011 A1 | 5/2004 | Patel et al. |
| 2004/0163001 A1 | 8/2004 | Bodas |
| 2004/0189161 A1 | 9/2004 | Davis et al. |
| 2004/0221287 A1 | 11/2004 | Walmsley |
| 2004/0240514 A1 | 12/2004 | Bash et al. |
| 2004/0242197 A1 | 12/2004 | Fontaine |
| 2004/0262409 A1 | 12/2004 | Crippen et al. |
| 2005/0023363 A1 | 2/2005 | Sharma et al. |
| 2005/0033889 A1 | 2/2005 | Hass et al. |
| 2005/0063542 A1 | 3/2005 | Ryu |
| 2005/0102674 A1 | 5/2005 | Tameshige et al. |
| 2005/0108720 A1 | 5/2005 | Cervini |
| 2005/0132376 A1 | 6/2005 | Rodgers et al. |
| 2005/0154507 A1 | 7/2005 | Pierro et al. |
| 2005/0225936 A1 | 10/2005 | Day |
| 2005/0228618 A1 | 10/2005 | Patel et al. |
| 2005/0240745 A1 | 10/2005 | Iyer et al. |
| 2005/0267639 A1 | 12/2005 | Sharma et al. |
| 2006/0047808 A1 | 3/2006 | Sharma et al. |
| 2006/0080001 A1 | 4/2006 | Bash et al. |
| 2006/0095911 A1 | 5/2006 | Uemura et al. |
| 2006/0096306 A1 | 5/2006 | Okaza et al. |
| 2006/0112286 A1 | 5/2006 | Whalley et al. |
| 2006/0115586 A1 | 6/2006 | Xing et al. |
| 2006/0121421 A1 | 6/2006 | Spitaels et al. |
| 2006/0139877 A1 | 6/2006 | Germagian et al. |
| 2006/0168975 A1 | 8/2006 | Malone et al. |
| 2006/0179436 A1 | 8/2006 | Yasue |
| 2006/0214014 A1 | 9/2006 | Bash et al. |
| 2007/0019569 A1 | 1/2007 | Park et al. |
| 2007/0038414 A1 | 2/2007 | Rasmussen et al. |
| 2007/0074222 A1 | 3/2007 | Kunze |
| 2007/0078635 A1 | 4/2007 | Rasmussen et al. |
| 2007/0083870 A1 | 4/2007 | Kanakogi |
| 2007/0121295 A1 | 5/2007 | Campbell et al. |
| 2007/0150215 A1 | 6/2007 | Spitaels et al. |
| 2007/0171613 A1 | 7/2007 | Mcmahan et al. |
| 2007/0174024 A1 | 7/2007 | Rasmussen et al. |
| 2007/0180117 A1 | 8/2007 | Matsumoto et al. |
| 2007/0190919 A1 | 8/2007 | Donovan et al. |
| 2007/0213000 A1 | 9/2007 | Day |
| 2007/0226741 A1 | 9/2007 | Seshadri |
| 2007/0260417 A1 | 11/2007 | Starmer et al. |
| 2007/0274035 A1 | 11/2007 | Fink et al. |
| 2008/0041076 A1 | 2/2008 | Tutunoglu et al. |
| 2008/0104604 A1 | 5/2008 | Li et al. |
| 2008/0104985 A1 | 5/2008 | Carlsen |
| 2008/0105412 A1 | 5/2008 | Carlsen et al. |
| 2008/0115140 A1 | 5/2008 | Erva et al. |
| 2008/0133474 A1 | 6/2008 | Hsiao et al. |
| 2008/0134191 A1 | 6/2008 | Warrier et al. |
| 2008/0162983 A1 | 7/2008 | Baba et al. |
| 2008/0174954 A1 | 7/2008 | Vangilder et al. |
| 2008/0180908 A1 | 7/2008 | Wexler |
| 2008/0186670 A1 | 8/2008 | Lyon et al. |
| 2008/0209243 A1 | 8/2008 | Ghiasi et al. |
| 2008/0216074 A1 | 9/2008 | Hass et al. |
| 2008/0216076 A1 | 9/2008 | Udell et al. |
| 2009/0030554 A1 | 1/2009 | Bean, Jr. et al. |
| 2009/0049447 A1 | 2/2009 | Parker |
| 2009/0094481 A1 | 4/2009 | Vera et al. |
| 2009/0138313 A1 | 5/2009 | Morgan et al. |
| 2009/0138888 A1 | 5/2009 | Shah et al. |
| 2009/0150123 A1 | 6/2009 | Archibald et al. |
| 2009/0150129 A1 | 6/2009 | Archibald et al. |
| 2009/0150700 A1 | 6/2009 | Dell'era |
| 2009/0150893 A1 | 6/2009 | Johnson et al. |
| 2009/0171511 A1 | 7/2009 | Tolentino |
| 2009/0199019 A1 | 8/2009 | Hongisto et al. |
| 2009/0205416 A1 | 8/2009 | Campbell et al. |
| 2009/0217277 A1 | 8/2009 | Johnson et al. |
| 2009/0223234 A1 | 9/2009 | Campbell et al. |
| 2009/0259343 A1 | 10/2009 | Rasmussen et al. |
| 2009/0265568 A1 | 10/2009 | Jackson |
| 2009/0309570 A1 | 12/2009 | Lehmann et al. |
| 2009/0326879 A1 | 12/2009 | Hamann et al. |
| 2009/0326884 A1 | 12/2009 | Amemiya et al. |
| 2010/0010688 A1 | 1/2010 | Hunter |
| 2010/0031259 A1 | 2/2010 | Inoue |
| 2010/0100877 A1 | 4/2010 | Greene et al. |
| 2010/0106464 A1 | 4/2010 | Hlasny et al. |
| 2010/0139908 A1 | 6/2010 | Slessman |
| 2010/0146316 A1 | 6/2010 | Carter et al. |
| 2010/0153956 A1 | 6/2010 | Capps, Jr. et al. |
| 2010/0174886 A1 | 7/2010 | Kimelman |
| 2010/0180089 A1 | 7/2010 | Flemming et al. |
| 2010/0217454 A1 | 8/2010 | Spiers et al. |
| 2010/0241285 A1 | 9/2010 | Johnson et al. |
| 2010/0241881 A1 | 9/2010 | Barsness et al. |
| 2010/0256959 A1 | 10/2010 | Vangilder et al. |
| 2010/0269116 A1 | 10/2010 | Potkonjak |
| 2010/0286956 A1 | 11/2010 | Vangilder et al. |
| 2010/0287018 A1 | 11/2010 | Shrivastava et al. |
| 2010/0293313 A1 | 11/2010 | Ferringer et al. |
| 2010/0313203 A1 | 12/2010 | Dawson et al. |
| 2010/0324739 A1 | 12/2010 | Dawson et al. |
| 2010/0324956 A1 | 12/2010 | Lopez et al. |
| 2011/0016339 A1 | 1/2011 | Dasgupta et al. |
| 2011/0035078 A1 | 2/2011 | Jackson |
| 2011/0038634 A1 | 2/2011 | Decusatis et al. |
| 2011/0040529 A1 | 2/2011 | Hamann et al. |
| 2011/0055605 A1 | 3/2011 | Jackson |
| 2011/0072293 A1 | 3/2011 | Mazzaferri et al. |
| 2011/0107332 A1 | 5/2011 | Bash |
| 2011/0161696 A1 | 6/2011 | Fletcher |
| 2011/0173470 A1 | 7/2011 | Tran |
| 2011/0213508 A1 | 9/2011 | Mandagere et al. |
| 2011/0246995 A1 | 10/2011 | Fedorova et al. |
| 2011/0271283 A1 | 11/2011 | Bell, Jr. et al. |
| 2011/0283119 A1 | 11/2011 | Szu et al. |
| 2011/0296212 A1 | 12/2011 | Elnozahy et al. |
| 2011/0302582 A1 | 12/2011 | Jacobson et al. |
| 2012/0005683 A1 | 1/2012 | Bower et al. |
| 2012/0053778 A1 | 3/2012 | Colvin et al. |
| 2012/0071992 A1 | 3/2012 | Vangilder et al. |
| 2012/0072916 A1 | 3/2012 | Hintermeister et al. |
| 2012/0079235 A1 | 3/2012 | Iyer et al. |
| 2012/0079380 A1 | 3/2012 | Tsai et al. |
| 2012/0084790 A1 | 4/2012 | Elshishiny et al. |
| 2012/0109391 A1 | 5/2012 | Marwah et al. |
| 2012/0131309 A1 | 5/2012 | Johnson et al. |
| 2012/0158387 A1 | 6/2012 | Vangilder et al. |
| 2012/0170205 A1 | 7/2012 | Healey et al. |
| 2012/0180055 A1 | 7/2012 | Brech et al. |
| 2012/0210325 A1 | 8/2012 | De Lind Van Wijngaarden et al. |
| 2012/0216065 A1 | 8/2012 | Nastacio |
| 2012/0216190 A1 | 8/2012 | Sivak |

(56) References Cited

U.S. PATENT DOCUMENTS

| | | |
|---|---|---|
| 2012/0216205 A1 | 8/2012 | Bell, Jr. et al. |
| 2012/0221872 A1 | 8/2012 | Artman et al. |
| 2012/0266174 A1 | 10/2012 | Inoue |
| 2012/0278810 A1 | 11/2012 | Dawson et al. |
| 2012/0290862 A1 | 11/2012 | Brown et al. |
| 2012/0323393 A1 | 12/2012 | Imhof et al. |
| 2013/0006426 A1 | 1/2013 | Healey et al. |
| 2013/0061236 A1 | 3/2013 | Ghose |
| 2013/0066477 A1 | 3/2013 | Jiang |
| 2013/0104136 A1 | 4/2013 | Brech et al. |
| 2013/0124003 A1 | 5/2013 | Lehman |
| 2013/0132972 A1 | 5/2013 | Sur et al. |
| 2013/0139170 A1 | 5/2013 | Prabhakar et al. |
| 2013/0166885 A1 | 6/2013 | Ramani et al. |
| 2013/0178991 A1 | 7/2013 | Gheerardyn et al. |
| 2013/0178993 A1 | 7/2013 | Rombouts et al. |
| 2013/0245847 A1 | 9/2013 | Steven et al. |
| 2013/0290955 A1 | 10/2013 | Turner et al. |
| 2013/0304903 A1 | 11/2013 | Mick et al. |
| 2013/0346139 A1 | 12/2013 | Steven et al. |
| 2013/0346987 A1 | 12/2013 | Raney et al. |
| 2014/0039965 A1 | 2/2014 | Steven et al. |
| 2014/0046908 A1 | 2/2014 | Patiejunas et al. |
| 2014/0047261 A1 | 2/2014 | Patiejunas et al. |
| 2014/0047266 A1 | 2/2014 | Borthakur et al. |
| 2014/0059556 A1 | 2/2014 | Barsness et al. |
| 2014/0074876 A1 | 3/2014 | Venkataramani et al. |
| 2014/0075448 A1 | 3/2014 | Bell, Jr. et al. |
| 2014/0129779 A1 | 5/2014 | Frachtenberg et al. |
| 2014/0136625 A1 | 5/2014 | Graham et al. |
| 2014/0164700 A1 | 6/2014 | Liang |
| 2014/0229221 A1 | 8/2014 | Shih et al. |
| 2014/0237090 A1 | 8/2014 | Lassen et al. |
| 2014/0257907 A1 | 9/2014 | Chen et al. |
| 2014/0278692 A1 | 9/2014 | Marwah et al. |
| 2014/0310427 A1 | 10/2014 | Shaw et al. |
| 2014/0330611 A1 | 11/2014 | Steven et al. |
| 2014/0330695 A1 | 11/2014 | Steven et al. |
| 2015/0012710 A1 | 1/2015 | Liang et al. |
| 2015/0019036 A1 | 1/2015 | Murayama et al. |
| 2015/0026695 A1 | 1/2015 | Dawson et al. |
| 2015/0057824 A1 | 2/2015 | Gheerardyn et al. |
| 2015/0066225 A1 | 3/2015 | Chen et al. |
| 2015/0088576 A1 | 3/2015 | Steven et al. |
| 2015/0112497 A1 | 4/2015 | Steven et al. |
| 2015/0161199 A1 | 6/2015 | Pinko |
| 2015/0177808 A1 | 6/2015 | Sarti |
| 2015/0186492 A1 | 7/2015 | Shalita et al. |
| 2015/0234441 A1 | 8/2015 | Jackson |
| 2015/0235308 A1 | 8/2015 | Mick et al. |
| 2015/0278968 A1 | 10/2015 | Steven et al. |
| 2015/0317349 A1 | 11/2015 | Chao et al. |
| 2016/0019093 A1 | 1/2016 | Dawson et al. |
| 2016/0055036 A1 | 2/2016 | Dawson et al. |
| 2016/0078695 A1 | 3/2016 | McClintic et al. |
| 2016/0087909 A1 | 3/2016 | Chatterjee et al. |
| 2016/0118790 A1 | 4/2016 | Imhof et al. |
| 2016/0179711 A1 | 6/2016 | Oikarinen et al. |
| 2016/0180474 A1 | 6/2016 | Steven et al. |

\* cited by examiner

Integrated control strategy for servers and cooling system

Current situation: servers operate at low energy-efficiency regions; more servers are active Situation with the use of proposed techniques: servers operate at higher energy-efficiency regions; fewer servers are active The server energy-efficiency improvement goals of the proposed effort

ENERGY AWARE PROCESSING LOAD DISTRIBUTION SYSTEM AND METHOD

CROSS REFERENCE TO RELATED APPLICATION

The present application is a Continuation of Ser. No. 17/543,122, filed Dec. 6, 2021, now U.S. Pat. No. 11,809,254, issued Nov. 7, 2023, which is a Division of U.S. patent application Ser. No. 15/694,459, filed Sep. 1, 2017, now U.S. Pat. No. 11,194,353, issued Dec. 7, 2021, which is a Continuation of U.S. patent application Ser. No. 14/153,540, filed January 134, 2014, now U.S. Pat. No. 9,753,465, issued Sep. 5, 2017, which is a Continuation of U.S. patent application Ser. No. 12/841,169, filed Jul. 21, 2010, now U.S. Pat. No. 8,631,411, issued Jan. 14, 2014, which claims benefit of priority from U.S. Provisional Patent Application No. 61/227,361, filed Jul. 21, 2009, each of which is expressly incorporated herein by reference in its entirety.

FIELD OF THE INVENTION

The present invention relates to the field of server energy and cooling management.

BACKGROUND OF THE INVENTION

The data center energy crisis has been in the making for the past several decades, as data centers are designed primarily with peak performance and peak capacity in mind. With the doubling of transistor counts and performance in semiconductor devices at 18-month intervals following Moore's law, energy dissipation in servers have grown at an alarming rate. The smaller form factors of modern blade servers have, at the same time, permitted more and more servers to be packed into a given physical space, further worsening the already critical situation with server power dissipations within data centers. Adding to all of this is the trend to overprovision data center capacities and the use of overrated power supplies for the individual servers. Such over provisioning results in gross energy inefficiencies as servers and power supplies are generally designed to give very high energy efficiencies only at or near peak loading levels. The net result of all of these is that 50% and upwards of the total cost of ownership (TCO) for a data center is in the utility costs of operating and cooling the servers. From an economic standpoint, we spend about 2% of the nation's annual energy consumption on data centers. With electricity costs growing annually at about 7% to 10%, the situation is bleak and needs immediate correction with the use of innovative and dramatic solutions. The other benefits of operating energy-efficient data centers are of no less significance—reducing the carbon footprint and making the nation energy-secure are also worthy goals.

Traditional approaches to managing the data center energy crisis have been to use advanced cooling and packaging solutions, to use DC power sources for servers and a variety of other solutions at reducing the energy dissipation within servers. These latter solutions have included the use of dynamically changing the power-performance settings for individual server components, such as processors and hard disk drives, or on policy-based job scheduling that schedule the offered workload across servers to meet thermal objectives. The growing use of virtualization technologies in data center also supports flexible scheduling based energy management schemes. Virtually, all of these solutions are reactive in nature: energy management or cooling solutions are adjusted based on the feedback from sensors that sense temperature or some activity parameter (such as current computing load, performance metrics).

SUMMARY OF THE INVENTION

The present technology assumes, according to one embodiment, a holistic view of data centers as a cyberphysical system where the cooling solutions work in unison with the computing level solutions for energy management in a coordinated fashion. The total energy expended in the computing components and the energy expended in the cooling system is treated as a first class resource that needs to be scheduled explicitly to maximize the overall energy-efficiency of the data center. One embodiment of aspects of the technology is multi-tiered and includes:

The use of fast models for predicting local and global thermal conditions to promote overall energy efficiency. The thermal models, in turn, are driven by empirical models of energy dissipation within servers and switches as a function of the measured values of a variety of actual activity counts. This approach of jointly using accurate energy dissipation models for the computing equipment and fast thermal models permit the cooling solutions (adjustment of inlet temperature, air flow speed and pattern) to be proactive.

The use of a global scheduler to allocate individual energy budgets to servers as a function of the workload, the predicted thermal trend, actual server utilizations and temperature and airflow measurements from sensors. The cooling efforts are also matched to the predicted thermal trends and are rack specific, instead of being rack agnostic, as in traditional systems. Alternatively stated, the cooling efforts for a rack are directed, dynamic and matched to the thermal conditions in the rack's environment. This results in the most energy-efficient use of the cooling resources.

The use of modified server operating system kernels that permit the individual servers to stay within their assigned energy consumption budget. Software solutions at the operating system kernel level exercise existing power management actuators inside the processor and other components of servers in a proactive fashion to stay within the dictated energy budget and in a reactive fashion based on the thermal condition of its environment. Thus, the system uses a predictive model of the thermal conditions based on analysis of a set of "tasks" or other prospective activities, as well as a feedback driven control which employs sensors or indicia or actual conditions. The predictive model may be adaptive, that is, the predictive model may be modified in dependence on the actual outcomes as determined by the sensors or indicia. In addition to the sensor or indicia inputs, the system may also receive a price or cost input, which permits a price or cost optimization, rather than an efficiency optimization. By imposing an external price or cost consideration, the system can be made responsive to peak energy demand considerations, and also a prioritization of tasks, which may each be associated with a task value.

Each of these technologies may be employed together, separately, or in subcombination. The thermal models, for example, can be implemented with minor modification to semiconductor devices, to provide software access to registers and counters which monitor operation of the chip. As the chip processes information, various types of activities are tracked, and these tracked activities may then be read by software to implement the models. The models may be executed on the same semiconductor as an additional process within a multitasking processing stream, within a special core dedicated to this process, either on or off the integrated circuit, or by a remote system. The modified server operating system kernels typically do not require hardware modifications, though sensors may be required beyond those present in standard components of the computing system. In particular, integration and interfacing of external cooling system sensors and controls may require additional hardware modules. The global scheduler is typically provided as part of a load distribution switch, which is a standard hardware component, but executes software in accordance with the present embodiments. In particular, the task allocation algorithm favors loading of servers to near capacity, which may be defined by performance limitations or thermal limitations, before allocating tasks to other servers. The allocation may distinguish between different blades within a rack, with each rack typically being controlled on a thermal basis, i.e., to stay within a desired thermal envelope while achieving cost-efficient cooling, while each blade may be allocated tasks which balance performance and energy efficiency, while remaining within safe thermal limits.

The net result of a combination of all of this is a control system that uses a combination of proactive and reactive elements in a multi-tiered strategy for co-managing the thermal and computing solutions for promoting the energy efficiency (or cost effectiveness) of the data center. However, these technologies need not be employed together to gain benefits. Likewise, the chip, operating system (software), and system level optimizers need not communicate with each other, though they are preferably aware of the multi-level optimizations, which may alter responses to conditions. For example, a prediction of and control over future processing load must be coordinated between the various system levels in order to avoid conflicting efforts or overcompensation.

A preferred embodiment may be implemented in a scaled down data center consisting of Linux server racks with floor plenum and portable computer room air conditioners (CRACs) and a variety of sensors, or a full data center with server racks in a facility with centrally or distributed control cooling system. Preliminary results indicate that the present approach can realize about a 20% improvement in the energy efficiency of the data center.

Typical server installations use a large number of server machines to accommodate a typical set of incoming requests. Such installations use a single or a series of load balancing switches (also called front-end switches) to direct the incoming requests to the servers. The policies implemented for such directions are oblivious of the energy implications and focus primarily on the performance goals (latency, uniform loading etc.). Typical servers are designed to be most energy-efficient at or near their peak load settings and the average loading on individual servers with a processing load distributed in accordance with typical load balancing switch algorithms are generally well below the peak load levels. Consequently, servers operate at low energy-efficiency levels for most of the time.

According to an embodiment of the present invention, the front-end load balancing switches are made aware of the processing load level, energy dissipation levels and local temperatures (or other thermal-related variable) for each server. The firmware on these switches include an algorithm to only keep a minimum number of servers active, with each such active server operated at or near their peak load levels (and thus at very high energy-efficiency levels), to handle the current set of jobs. As the job demands grow, additional servers are bought on-line (recruited) from their inactive state; as demands shrink, more servers are de-activated to save power. In some cases, an asymmetric architecture is provided, in which servers having different load-efficiency characteristics are employed.

For low loads, it may be optimal to have a minimum number of servers available, even if these are operating below energy-optimal loading, since the loading is a statistical process, and the time to activate a server may induce significant latencies, while the turn-on and turn-off inefficiencies may dominate if the system operates near a threshold. Thus, as the processing load grows, one or more lower processing capacity servers may be replaced with a same or lesser number of higher capacity servers.

The load balancing switch can also direct cooling selectively towards the active servers. This can be done, for instance, by regulating airflow using louvers or vents, by increasing airflow near the active servers, by activating and controlling localized air conditioning units mounted on the racks or adjacent to racks.

In some cases, heat produced by a server system can be used to heat a facility. Typically, in a large facility, the heat produced is in excess of that required for the facility, or the efficiency of utilizing the waste heat is low. The remaining heat is shed to the exterior, for example by directly venting hot air flows, heat pumps (e.g., air conditioners), or waster cooling systems. Any harvesting of the waste heat may, of course, be considered in the allocation decisions, including the efficiency of the harvesting and its net cost benefit.

The logic for the switch can also be enhanced to determine an increase in the offered load by examining the occupancies of the incoming queues associated with the input ports of the switch and the rate at which they change. This information can be used to activate standby servers in advance. Additionally, idle servers can be started up and moved into the standby mode in anticipation of the increase in offered workload. The same mechanism can be used to deactivate servers if the offered workload decreases.

The switch logic, which may be internal to a switching device, or provided externally, may be further enhanced to accept utilization data from the active server and make use of it (optionally with the above sensed input queue sizes) to decide if the offered workload is increasing or decreasing and to eventually activate/deactivate servers (as before) based on the detected workload trend.

For example, a lesser capacity server may have a lower clock rate CPU, slower memory and bus speeds, lower power (and slower) local hard drive, and/or lower speed network connection. Thus, the load balancing switch algorithm need not model each increment in capacity as being a linear increase over a prior one, and indeed may optimize allocation of a task to a respective resource, e.g., server, based on the characteristics of the available resources, including their power consumption and thermal environment, as well as processing capacity. Advantageously, the load balancer optimizes the headroom of the system after allocation of the task, so that subsequent tasks can be efficiently allocated as well on a statistical basis.

Virtualization technology may be used, if needed to make the server system appear as a set of homogeneous servers, even if it is not. Likewise, cloud computing technologies may be employed on a cost-efficiency and/or energy optimal basis. Typically, cloud computing systems do not provide transparency over the exact destination of a task, thus making energy efficiency consideration difficult. However, such systems generally have an economic cost of use. Therefore, a balancing algorithm may calculate an equivalent cost for incremental load, and use a cloud-type system for incremental usage which would be inefficiently performed locally. For example, a compute task which leaves a server 95% underutilized might be cost inefficient, and better offloaded to an external system, even if the incremental cost as compared to a local, fully loaded server is relatively high.

Additional features built into the modified switch firmware can activate or deactivate servers, taking into account performance goals and temperature trends, based on, for example, incoming queue sizes to switch and their growth or shrink rate, utilization of active servers, as measured by the OS, temperature data sensed directly or indirectly, and air flow (or other cooling facility) data. To prevent frequent activation and deactivation of individual servers, a few servers are maintained in a standby state before they are switched off. Alternatively or additionally, the number of requests in the incoming queues of the front-end switch ports can be used to anticipate the load level of the server and drive server activation/deactivation. As discussed above, the potential availability of an external resource may also be considered when determining whether a server is activated or deactivated.

Servers typically have a maximum specified operating temperature, above which damage may occur. On the other hand, processor manufacturers in some cases permit systems or system components to exceed steady state maximum power dissipation for short periods, in order to increase peak performance. On a large system basis, therefore, thermal monitoring and reaction is useful or necessary, especially for a server rack running at full load, and thus high thermal dissipation. The temperature of a rack is dependent on many factors, relating to both heat generation, and heat dissipation. The heat generation may be estimated by the load balancing (or in this case, load allocation) switch by profiling the tasks to be performed, and a statistically and empirically determined amount of power which is consumed by that task.

The heat dissipation characteristics of a real system are quite complex to predict, and even subtle changes can influence the result. Heat dissipation is dependent on temperature difference, air-flow patterns, cooling air temperature, etc. In a rack of equipment with a reasonably high load (but not at peak load), under reasonably constant thermal dissipation conditions, an incremental increase in energy consumption as a result of execution of a more demanding task, will likely lead to an increased temperature. Note, however, that internal feedback and control systems within a server, system, or rack may alter these presumptions.

The system may include various types of sensors. For example, board and system level components may have intrinsic thermal sensing capability that can be read by software, and passed on to the switches. Additional sensors can be provided which are interfaced through individual servers, or provided as a separate sensing network. The switch can received processed data representing temperatures and/or energy consumption and/or energy consumption per time interval from individual computing systems, or it may receive unprocessed or minimally processed data which is then processed and calibrated at the switch level. The switch therefore can use the data to schedule tasks within a across a plurality of servers, and/or adjust the performance settings of the servers and/or adjust the cooling directed at individual racks or servers.

For example, a thermally responsive fan will spin faster when the sensor indicates a higher temperature, thus violating a presumption of constant thermal dissipation characteristics. On the other hand, if the system is loaded with a statistical balance of tasks, there will more generally be a proportionality between increasing tasks and increasing temperature. Therefore, the load allocation server receives a temperature (or other relevant thermal variable) input, since a server operating at peak temperature should probably not receive further tasks, except to replace those which complete. Likewise, an analysis of the server may indicate that components of the server system are underutilized, and thus an increase in task load which implicate those components would result in a lesser increase in thermal load than those which are fully utilized, especially the processor(s).

Therefore, as a server approaches its maximum temperature, the load allocation server may select those tasks, which incur low incremental thermal load yet make use of resources within the server which are available for additional use. On the other hand, servers which are below their peak temperature, for example a server which is just being activated, may be allocated tasks which cause relatively high thermal dissipation, and thus would be inappropriate for a "hot" server. It is also noted that thermal dissipation increases with thermal differential, and therefore a hot server or rack is more efficiently cooled by a flow of air at a constant temperature as compared to a cooler server. To the extent that the heat can be dissipated externally by convection or radiation, and not simply shed by a heat pump (e.g., air conditioner), the loading of servers to achieve maximum temperatures is also an advantage. As stated above, the total thermal dissipation is generally decreased for a highly loaded server system than for the same set of tasks distributed across a larger number of lightly loaded servers, and therefore even in the case of a heat pump cooled facility, the present system is more efficient.

Switches can use a combination of one or more of the following to decide how to schedule workload and activate or deactivate servers:

1) Incoming queue sizes to switch and their growth or shrink rate
2) Utilization of active servers, as measured by the OS
3) Temperature data sensed directly or indirectly.
4) Air flow (or other cooling facility) data In addition to workload scheduling, activating/deactivating servers, switch logic directs cooling effort to where it's needed. A cooling system model may be implemented to ensure that the cooling is achieved efficiently, and, for example, may provide cost-benefit data to the switch.

This technique has the potential for improving the energy-efficiency of server systems through relatively modest changes in the operating system kernel and front-end switch firmware. No reliance is required on custom hardware or dedicated hardware support. That is, the traditional load balancing switch is reconfigured/reprogrammed to be a load concentration switch, which predicts when a new server or bank of servers on a rack needs to be activated and/or deactivated, and optionally provides an ability to use external resources on a cost-efficiency basis.

The load allocation switch may further include an economic optimization which balances performance, which may be somewhat diminished by highly loading servers, with improvements in efficiency. Likewise, server lifetime and reliability are adversely affected by high operating temperatures, and is may also be treated as a cost. It is noted that the economic life of a server system is typically less than the mean time between failures of the system at maximum rated temperature, and therefore this cost may be relatively low. Likewise, the reliability cost incurred in operating one portion of the system at maximum load may be recovered, in whole or in part, by deactivating other servers. The allocation algorithm may rotate highly loaded servers, on one hand, to balance lifetime, or concentrate stresses on a single system, on the other. One reason for concentrating stresses is, for example, to focus maintenance efforts on a smaller number of systems which operate continuously, rather than on a large distributed system in which failures in any portion are equally probable.

It is therefore an object to provide a method for controlling a data center, comprising a plurality of server systems, each server system having an associated dynamically controllable cooling system and a predetermined thermal constraint, comprising: receiving an input corresponding to a concurrent physical condition of at least one of a first server system and an environment of the first server system; predicting a future physical condition based on a set of future states of the first server system; dynamically controlling the dynamically controllable cooling system in response to at least the input and the predicted future physical condition to selectively cool the first server system sufficient to meet the predetermined thermal constraint; and controlling an allocation of tasks between the plurality of server systems to selectively load the first server system within the predetermined thermal constraint and selectively idle a second server system, wherein the idle second server system is adapted to be enabled to accept tasks when allocated to it, and wherein the dynamically controllable cooling system associated with the idle second server system is selectively operated in a low power consumption state.

It is also an object to provide a system for controlling a plurality of servers, each server having an associated dynamically controllable cooling system and a predetermined thermal constraint, comprising: an interface port configured to receive an input corresponding to a concurrent physical condition of a first server system; and at least one processor, configured to: estimate a future physical condition based on a set of future states of the first server system; dynamically control the dynamically controllable cooling system in response to at least the input and the predicted future physical condition to selectively cool the first server system sufficient to meet the predetermined thermal constraint; and attempting to schedule tasks for the plurality of server systems to selectively load the first server system within the predetermined thermal constraint and selectively idle a second server system, wherein the idle second server system is configured to be recruited to accept tasks when allocated to it, and wherein the dynamically controllable cooling system associated with the idle second server system is selectively operated in a low power consumption state.

Each of the plurality of server systems may comprise a rack or server blades.

The associated dynamically controllable cooling system may comprise an air conditioner. The air conditioner may comprise a control adapted to vary an air flow rate and an air temperature or air for cooling the first server system. The air conditioner may be associated with a proportionally controllable baffle.

The predetermined thermal constraint may comprise a maximum operating temperature of at least one component of a server system. The predetermined thermal constraint may also comprise a maximum energy consumption of a server system.

The input may be received from a thermal sensor, sensing a temperature of a component within the first server system.

The input may comprise an energy consumption of at least one component within the first server system.

The future physical condition may comprise a temperature of at least one component within the first server system, the temperature being predicted based on a model of the first server system and a sequence of operations performed by the first server system.

The future physical condition may comprise a temperature of at least one component within the first server system, the temperature being predicted based on a model of the first server system, a sequence of operations performed at least one component of the first server system, and a control parameter which varies a performance of the at least one component.

The dynamically controllable cooling system may be controlled to produce increased cooling of the first server system after the predicted future physical condition indicates an increase in cooling demand and before an increase in temperature is indicated by the input.

The first server system may be controlled to operate near a maximum operating temperature before the idle second server is recruited.

A task may be allocated to the second server system when the first server system is at risk of exceeding the predetermined thermal constraint.

A task may be reallocated from the first server system to the second server system when the first server system is at risk of exceeding the predetermined thermal constraint.

The plurality of server systems may comprise a plurality of elements each adapted to execute a function, the plurality of elements differing in a respective energy consumption and performance, further comprising selectively distributing functions to respective ones of the plurality of elements to optimize an energy efficiency.

An aggregate energy consumption of the first server system and associated cooling system and idle second server system and associated cooling system may be less than an aggregate energy consumption if the tasks are equally allocated between the first and second server systems.

The cooling system associated with the idle second server system may be operated to consume less power than the cooling system associated with the first server system.

Each of the plurality of server systems may comprise a plurality of processing units, each processing unit executing under an operating system, wherein at least a portion of said predicting is executed as a part of the operating system.

Each of the plurality of server systems may comprise a plurality of processing units, each processing unit executing under an operating system, wherein at least a portion of said controlling is executed as a part of the operating system.

The plurality of server systems may be controlled by a centralized control adapted to allocate tasks between the server systems or portions thereof, in dependence on at least the input and the predicting.

The dynamically controlling the dynamically controllable cooling system and controlling an allocation of tasks between the plurality of server systems may cooperate to maximize energy efficiency of the plurality of server systems and their associated dynamically controllable cooling systems.

The method may further comprise receiving cost and benefit value factors, wherein the dynamically controlling the dynamically controllable cooling system and controlling an allocation of tasks between the plurality of server systems are optimize a cost-benefit operation of the plurality of server systems and their associated dynamically controllable cooling systems.

The at least one processor may receive cost and benefit value factors, and controls the dynamically controllable cooling system and an allocation of tasks between the plurality of server systems to optimize a cost-benefit operation of the plurality of server systems and their associated dynamically controllable cooling systems.

DETAILED DESCRIPTION OF THE PREFERRED EMBODIMENTS

Figure 1:
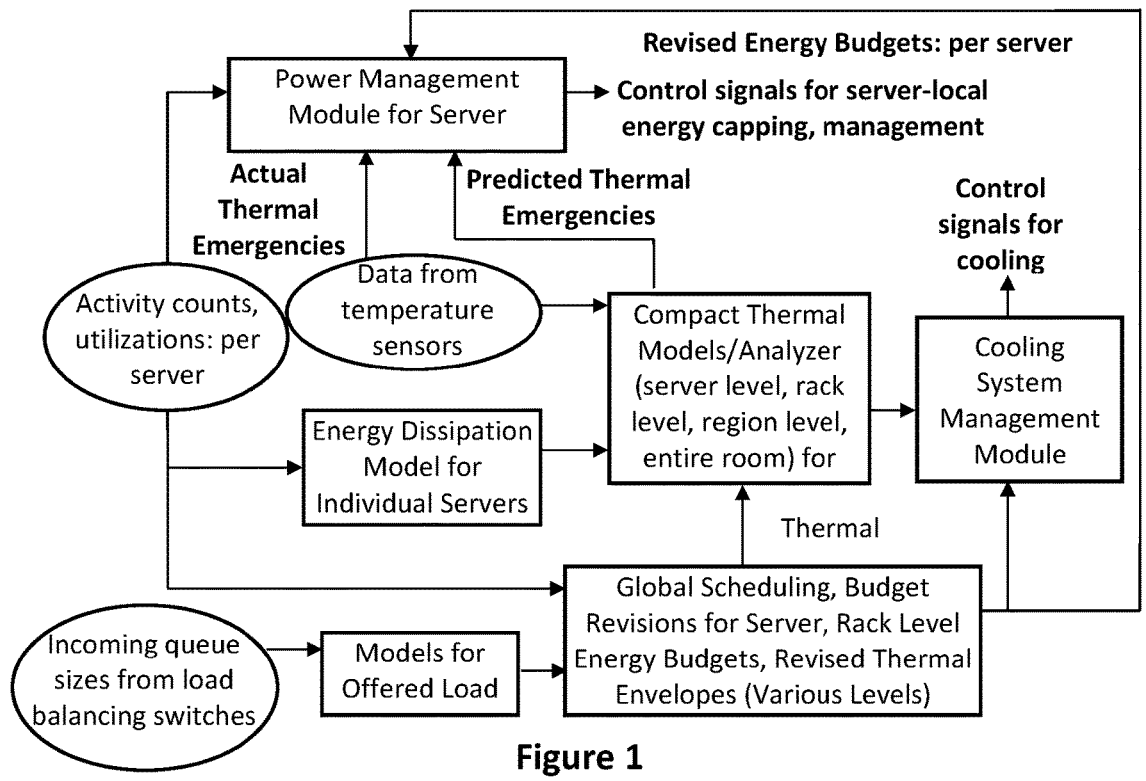
FIG. 1 depicts the control system aspects of the present data center management strategy.

According to a prototype embodiment, a scaled down data center is provided which demonstrates a unique approach to addressing the data center energy crisis. The energy spent on the computing equipment and by the cooling system is treated as a first class resource and managed explicitly in the present approach in a proactive as well as reactive manner. Instead of the traditional approach of cooling the server racks uniformly, dynamic and directed cooling is employed, that skews the cooling efforts to match the actual and projected cooling demands of the individual or groups of racks. Cooling for a rack is controlled based on sensors (i.e., a reactive control), a prospective set of tasks or functions in a queue (i.e., a proactive control), and an operating system component of each subsystem which permits a modification of energy demand.

It is noted that a cooling system may have higher efficiency when cooling a relatively hotter server than a cooler one, and therefore overall efficiency may be increased by permitting some server racks to run near a maximum operating temperature, and other racks to be essentially deactivated, pending peak demand recruitment. While running at relatively higher temperatures may be a factor in reducing a mean time between failures (MBTF), the usable life of blades in a data center is typically well in excess of the economic life; further, even if there is a failure, the data center will typically have automatic failover fault tolerance systems. Indeed, if some racks in the data center are specifically designed to always run near peak capacity and high temperature, these may be configured for more efficient operation, for example, greater spacing from other racks, to permit better heat load shedding without affecting adjacent racks, and higher temperature specification components.

It is also noted that in some cases, it is not the temperature per se which adversely impacts the MBTF of a system, but rather the thermal cycling and mechanical stresses on components, circuit boards, and packaging. In such cases, the operation of a rack at a consistent hot temperature may be an advantage over a system which seeks, for example, a uniform minimum temperature of all racks which varies with data center load.

One embodiment of the technology improves the overall energy-efficiency of a data center in a holistic manner, and targets both the energy expended in operating the equipment and the energy expended in the cooling system. A key aspect of is to coordinate the activities of all of the energy consumers in a data center. These consumers include the individual severs and communication infrastructures as well as the cooling system components. Some current solutions to this problem have addressed inefficiencies in the use of power conversion devices, the cooling system and the servers themselves [Sh 09, BH 07, BH 09, LRC+08]. Emerging solutions to this problem have also started to address the need to coordinate the activities of these consumers [BH 09, NSSJ 09, SBP+05, TGV 08]. As an example, the work of [TGV 08] has proposed an approach for minimizing the energy expended on the cooling equipment by minimizing the inlet temperature through appropriate job scheduling. The work of [NSSJ 09] coordinates the energy expended on the computing equipment and the cooling infrastructures and allocates energy budgets to virtual machines. Such VM energy budgets are not easy to implement, as energy expended by a VM is not easy to track and control; energy dissipation in many related components are ignored in simplifications that are used. In general, emerging solutions have a number of potential limitations:

The energy and performance overhead associated with job rescheduling and VM management and server-local scheduling overhead are ignored. The communication infrastructures within a data center are heavily utilized and are prone to congestion, resulting in significant added energy dissipation if jobs are rescheduled.

A simple rescheduling of the jobs may not make the most energy-efficient use of the servers and racks—the operating configurations of such servers have to be continuously adapted to fit the characteristics of the workload.

Simple reactive control systems, as proposed in all existing and emerging solutions, do not address the problem of thermal lags and delays associated with temperature sensors, whose inputs are used by the actuators in these systems.

The implicit assumption in most current systems that that all servers and racks have a uniform external cooling requirement may not be the best one for improving overall energy efficiency. While we do have some proportional cooling facilities in the form of automatically adjusted CPU cooling fan and enclosure fan speeds, external cooling systems are generally uniform and oblivious of the specific cooling needs of an entire rack. In general, higher energy efficiency will result by redirecting additional cooling to regions that can benefit from it, resulting in a dynamic, directed cooling system.

The present approach allocates energy budgets to servers, racks, storage and communication components and adapts the cooling effort dynamically to match the energy dissipated in these components. The energy consumption in the computing components are modeled using accurate empirical formulas and server-local (and global) scheduling techniques are used to limit server energy consumption within the allocated budget. This is a far more practical approach compared to any scheme that operates on the basis of energy budget allocations to VMs. The energy dissipation estimates from these empirical models are used to schedule the energy budgets for the computing equipment and the dynamic cooling system, along with the workload. Last but not the least, the present control system uses both proactive and reactive control mechanisms to manage the data center effectively in the face of sudden workload variations and to mitigate latencies associated with the activation and deactivation of servers and VMs.

In current data centers, the software systems infrastructures (including the Linux OS and popular file systems) are very limited in their adaptation capabilities in this respect. The most popular mechanism used for adaption is dynamic voltage and frequency scaling (DVFS) on the processing cores, and other components of the computing platform are unaddressed. This is not a desirable situation from the standpoint of energy efficiency, as the total of the energy dissipations within the DRAM modules and in the backplane and other communication infrastructures is about 45% of the total energy expended by a server, while the processors consume about 30% of the total energy [BH 09]. Current measurements seem to indicate that the processor energy dissipation will continue to decrease relative to the energy dissipation within the other components of a server [BH 09]. At the server level, it is thus critical to incorporate mechanisms that address the energy dissipation across all major components of a server instead of just focusing on the processing cores.

At the data center level, the energy expended in the communication infrastructures (switches, in particular) and in the cooling system itself should be considered. The present approach considers the total energy expended in the computing, storage, communications and cooling system as an explicitly scheduled resource and to schedule the computing and cooling resources using a common framework. The end goal is to maximize the energy efficiency of the data center, consistent with the performance goals. As discussed above, a cost optimization paradigm may also be implemented. In a cost optimization, the costs and benefits are normalized, and a set of conditions with a maximum net benefit is selected. The costs in this case may be energy costs, though other costs can also be considered in the calculation, such as maintenance costs, operating costs, license fees, etc. The benefits are typically considered as the net work output of the system, e.g., computing results, though values may be placed on the speed, latency, accuracy and completeness, etc. of the result. Indeed, assuming the same computational task, the result may be worth more to some users than others. Thus, the energy efficiency considerations may be modified or distorted based on a variety of extrinsic factors. The cost optimization factors may be analyzed in a centralized controller, which permits an allocation of tasks at a scheduler or load balancer element, distributed to the various processing cores and made part of the modified operating system kernel, or a hybrid approach. Of course, other elements may also provide these functions. Example Use: Integrated, Dynamic Management of Computing and Cooling Resources The system preferably makes the best use of the energy expended in operating the computing and communication equipment as well as the energy expended in the cooling system. The energy expended by the computing and communication equipment and the cooling system is considered a first class resource and managed explicitly. Servers are allocated individual energy budgets and a modified Linux kernel in the servers is used to dynamically adjust the system settings and perform a local scheduling to stay within the individual server's energy budget allocation. The computation of the energy budgets for servers/racks and the control of the cooling system to effectively define a thermal envelope (that is, cap) for each server/rack for is done by a global module that senses a variety of conditions, as described later, to direct global job scheduling and to control the cooling system components, skewing the cooling effort across racks and regions as needed to improve the overall efficiency of the cooling system.

Another distinguishing feature of a preferred embodiment of the system is in its use of three controls for adapting a cooling system: the air flow rate directed at the racks from portable CRACs, the inlet temperature and the use of movable baffles to redirect air flow. Traditional solutions have largely looked at one or two of these adaptation techniques (mostly inlet temperature and somewhat rarely, air flow rate).

Using the terminology of [RRT+08], the integrated data center management technique is essentially a control system with the following components critical to the management:

Sensors: On the thermal/mechanical side, the sensors monitor the temperature and air flow rates in various parts of the rack and the room. On the computing side, the sensors are in the form of hardware instrumentation counters within the processing cores, counters for device and system utilizations maintained by the operating systems, variables that record the incoming queue size and others.

Actuators: Our management policy exercises various actuators to adapt the cooling system and the servers. On the thermal/mechanical side, the actuators adjust fan rates for regulating the air flow from CRACs, operate servo motors to adjust the baffles for air flow direction and use electromechanical subsystems to adjust the inlet temperature. On the computing side, the software elements used as actuators (a) control the voltage and frequency settings of the cores and activate/deactivate individual cores to ensure that they do not exceed their allocated energy budget and to respond to thermal emergencies at the board/component level; (b) schedule ready processes assigned to a server and adjust core settings (using (a)) to maximize the energy efficiency of the server; (c) perform global task scheduling and virtual machine activation, migration and deactivation based on the dynamically computed thermal envelopes and rack/server level energy budgets.

Controllers: The control policy itself will be comprised of two parts; the proactive and reactive, which are described in detail below.

FIG. 1 depicts the control system aspects of one embodiment of a data center management strategy. This control system uses a combination of proactive and reactive strategies:

Proactive strategies: two different types of dynamic proactive management of data centers are provided. These are:

1. Because of thermal lags, temperature sensors are unable to detect the onset of thermal emergencies due to sudden bursty activities with the server components, including those within the DRAM, cores, local (swap) disks, if any, and the network interfaces. Empirical power models for the server energy dissipation are therefore derived, using activity counters maintained within the Operating System and the built-in hardware instrumentation counters, as described below. The estimate of the energy dissipation of an individual server is based on sampled estimations of the activities (similar to that described in [PKG 01]). This estimate of the energy dissipated by a server within a sampling interval is used to guide local scheduling and control the local system settings. The estimates of the server energy dissipations within a rack are also used as the inputs to a fast, optimized and calibrated thermal model that provides data on the thermal trends, taking into account the environmental conditions. The computed thermal trends are used, in turn, to guide global and rack level job scheduling and VM management as well as to proactively direct cooling efforts towards a region of rising temperature/hot spot.

2. The front end queues of the switches used for load balancing are a good indicator of the offered computing load to a server. These queues are therefore monitored to proactively schedule new jobs in a manner that improves the overall energy efficiency of the data center. This proactive monitoring of the input queue also permits absorption of some of the latencies involved in activating racks and servers that are in a standby mode, as well as to absorb some of the latencies in VM migration. In fact, as described below, the proactive monitoring of the incoming queues of the load balancing switches also permits activation/deactivation and migration of VMs, taking into account the energy overhead of such management.

Reactive Strategies: The reactive strategies include the following sub strategies:

1. A management system to ensure that the energy consumption of the individual servers does not exceed their dictated energy budget. This subsystem controls the computing components as well as the network interface. This management system is part of the modified Linux kernel of the servers that uses a server power estimation model and the sampled value of the instrumentation counters found in modern microprocessors and other statistics maintained by the kernel to control system settings (including the DVFS settings).

2. A subsystem within the kernel that reacts to local and neighborhood thermal emergencies or trends, as detected from local/neighborhood temperature sensors as well as information generated by the fast thermal models/analyzer to either shut down individual servers/racks or to reconfigure server settings to reduce their energy dissipation. This subsystem is an added protection mechanism that works in conjunction with the other energy management systems—both reactive and proactive, and deals with high-impact unexpected emergencies such as CRAC failures.

3. In conjunction with (2) above, a subsystem that monitors the local/neighborhood thermal trends to allocate and direct local cooling capacity in a focused fashion to minimize energy consumption from the cooling system. This will operate on a slower time scale than the computing reactive strategies. The computing approach of (2) above and this thermal systems approach should operate synergistically to minimize the overall global energy usage while maintaining compute performance. The reactive controller will constantly tradeoff energy minimization between the computing and thermal systems activities.

4. A subsystem within the global budgeting module that reacts to global thermal emergencies based on sensed environmental conditions in the room and trend data computed by the fast thermal model/analyzer.

5. A subsystem within the global budgeting module that reacts to the data on actual server/rack utilizations to throttle down servers/racks as needed.

The overall goal of all of the control system elements, both proactive and reactive, is to maximize the overall system performance under the energy constraints dictated by the budgeting module. The budgeting module ensures that the relative components of the energy dissipated by the computing/communication elements and the cooling system are optimal.

Server Management

Figure 2A:
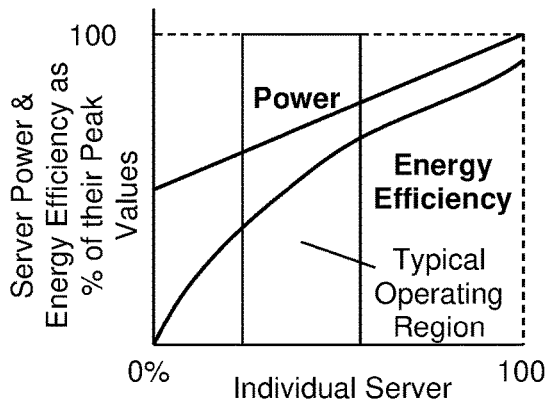
FIG. 2A depicts the state of affairs in prior art servers and shows how the power dissipation and energy efficiency of a typical server varies with server utilization.

The goal of our proposed effort is to improve the overall energy efficiency of the servers and the cooling system. To do this, we attempt to minimize the number of active servers and operate them at or near their peak loading level to maximize their energy efficiency. The existence of virtual machine support certainly makes this approach practical. At the same time, we minimize the energy consumption in the cooling system by just providing sufficient cooling for the active servers. FIG. 2A depicts the state of affairs in current servers and shows how the power dissipation and energy efficiency of a typical server varies with server utilization. As seen in FIG. 2A, the energy-efficiency is quite low at low server loading (utilization) and the power dissipation remains relatively high. FIG. 2A also depicts the typical operating points of servers—the typical average server loading is significantly lower than the peak loading—as a result, the overall energy efficiency is quite low at these typical operating points.

Figure 2B:
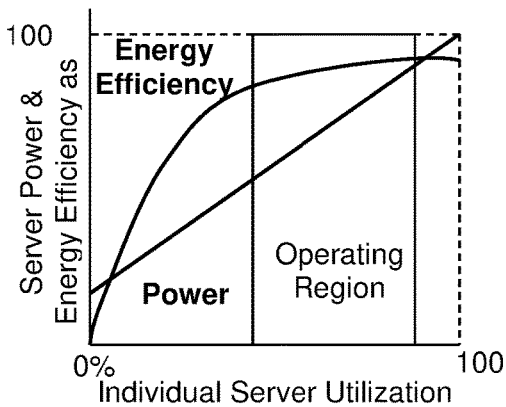
FIG. 2B depicts the intended overall impact of the present solution on server power dissipation and server energy efficiency plotted against server utilization.

FIG. 2B depicts the intended overall impact of the present technology on server power dissipation and server energy efficiency plotted against server utilization. The present multi-tiered server power management technique (which subsumes standard power management techniques) improves the server energy efficiency dramatically and simultaneously reduces the power dissipation at lower server utilization levels. The overall server efficiency thus remains quite high at the typical load levels and across a wider range of loading, as shown in FIG. 2B. Second, by globally scheduling more work to a fewer number of active servers (and by keeping the non-active servers in a standby state), we push the workload level on individual servers more towards a region where energy-efficiency is very high. The expected result of all of this is a solution that, based on a quick back-of-the-envelope calculation, can enhance the overall energy efficiency of servers by about 15% to 25% on the average beyond what is provided by the state-of-the-art, even when the added overhead of the present solution is factored in. Improvements in power savings are expected to be similar. One down side of operating servers at or near their peak capacity is that any sudden changes in the behavior of their assigned workload can cause switching activities to go up and lead to local thermal emergencies.

In general, servers can be more efficiently managed than presently feasible if they:

R1) Have mechanisms to put a hard limit on server energy dissipation to avoid thermal emergencies.

R2) Have a proactive mechanism to activate or deactivate virtual machines or servers or entire racks to match the offered load taking into account any energy and performance overhead for activation and deactivation.

R3) Have techniques that implement a more energy-proportional relationship between server power dissipation and the server utilization, as shown in FIG. 2B.

R4) Extend the operating region over which a server has high energy efficiency: this permits higher server energy efficiencies even at moderate load levels.

The implementation of requirements R3 and R4 lead to the situation shown in FIG. 2B. We now describe our approach to implementing these requirements in software on existing systems.

Implementing the Requirements R1 through R4

Empirical energy dissipation models are preferably used to determine the energy consumed by a server and this estimate is used to cap the energy consumed by a server.

This approach is adopted since it is not practical to use external power meters on each server to determine their energy consumption.

Empirical models for the energy dissipated by a server have been proposed in the past; the simplest of these models are based on the use of utilization data maintained by the operating system (such as core utilization, disk utilization) and is, for example, of the form:

$$P_{server} = K_0 + K_1 \times U_{proc} + K_2 \times U_{mem} + K_3 \times U_{disk} + K_4 \times U_{net}$$

Of course, other, more complex forms, may be employed.

Where the Ks are constants determined empirically and the Us refer to the utilizations of the processor ($U_{proc}$), memory ($U_{mem}$), the disk(s) ($U_{disk}$) and the network ($U_{net}$). The operating system maintains and updates these utilization data. As reported in [ERK+08], the actual measured power and the power estimated from the above equation are quite close and typically within 10%. A recent effort extends simplistic models of this nature to regression based predictive models that predict server energy consumption on long-running jobs as a function of the core energy dissipation, L2 cache misses and ambient temperature [LGT 08]. The model of [LGT 08] is a good starting point for our efforts. We will extend this model with additional metrics obtained from hardware instrumentation counters found in typical cores as well as slightly modified system calls for network/file I/O to account for energy dissipation within network components to accurately account for remote data access and inter-process communications and I/O activity (which were ignored in the work of [LGT 08]).

To track and predict the energy consumption of servers in software, sampled measurements of the hardware instrumentation counter values and OS-maintained counters for computing utilization will be used, in manner reminiscent of our earlier work of [PKG 01]. The modified thread scheduler in contemporary Linux kernels will use these sampled measurements to guide local scheduling within a server so as to limit the server energy consumption within a sampling period to stay within the limit prescribed by the global energy/workload scheduler. In additional to the traditional DVFS adjustments, the behavior of threads within the sampling periods will be classified as CPU bound, disk bound and network bound and schedule similar threads back-to-back to avoid unnecessary changes in the DVFS settings (and avoiding the energy overhead and relatively long latencies in changing such settings). This in turn addresses Requirements R3 and R4. The modified scheduler will also react to thermal emergencies as detected by external temperature sensors (which are read and recorded periodically by the scheduler itself on scheduling events within the kernel).

Requirement R2 is implemented in the global scheduler, as described below, by keeping track of the workload trends (through monitoring of the incoming request queues at the load balancing switches) and job completion statistics. If the global scheduler sees a growth in the job arrival rate, it activates VMs/servers/racks as needed to cope with the additional workload. The overhead for such activation and deactivation, including the energy costs of moving VM contexts are accounted for in this process, and thus requirement R3 is also addressed.

Techniques for message consolidation that packs several short messages into a single message within a jumbo Ethernet frame within the network interface to amortize the flat component of per-packet overhead of network transfers may also be employed. This also addresses Requirement R3.

A different way of amortizing the scheduling overhead (including the changing of the DVFS settings of cores) exploits the characteristics of repetitive jobs. In a typical server installation, the number of such jobs is expected to be quite high. For example, repetitive jobs of the SPECweb 2006 benchmarks on a Linux platform (with Intel E5460 cores) running Apache were dynamically classified into two classes: compute bound and I/O bound, based on utilization statistics maintained by the kernel and instruction commit rate data maintained in the hardware instrumentation counters. This classification data was maintained within the Apache server. Jobs of the same class in the work queue of Apache were scheduled back-to-back wherever possible and the DVFS settings of the dual core platform were explicitly controlled. Unnecessary changes in the DVFS settings were also avoided and job wait times on the queues were limited to maintain a performance level close to that of the base case. The CPU power measurements (made with a power clamp on the power cord for the core going from the power supply to the motherboard) showed that this simply strategy reduced the core power consumption by about 11%.

For the present system, this technique can be moved to the kernel level for added efficiency, extend the classification to add memory bound jobs (jobs that trigger a high proportion of RAM activity, as evidenced by the on-chip cache miss instrumentation counter) and network bound job classes, for instance. This classification information is used to schedule jobs that match the characteristics of processor sockets with a preset independent performance or to cores within a multicore chip that permits the use of similar preset performance settings independently for each core. The preset performance settings are changed only under load increases that saturate the capacity of a core with a specific DVFS setting. This approach of exploiting pre-classed job addresses requirements R3 and R4 simultaneously.

Global Energy Budget Allocation and Workload Scheduling

The global scheduler (GS) of a preferred embodiment of the system is responsible for the allocation of energy budgets for the VMs/servers/racks and the assignment of workload to the individual machines. The key requirement of the GS is that it has to be fast and scalable. The GS may be implemented on a few dedicated multicore machines which also implement the compact thermal analyzer and models. Multiple machines may be used to permit scalability; for a small server installation, it may be possible to implement all of the functions on a single multicore platform. These dedicated machines may also receive data from a variety of sources, which are optional, as shown in FIG. 1.

The GS maintains a variety of tables that record the energy/performance characteristics of each rack, its utilization statistics, and data on the environmental temperature computed from various sources. The GS also maintains a list of quality of service (QoS) requirements (guaranteed transaction rates, data delivery rates etc.) for implementing differentiated services. The GS also senses the incoming work queue sizes at the load balancing switches and uses simple workload models to predict the impact of incoming workload. The simple workload models can simply classify incoming jobs based on the request types or use more sophisticated information about pre-classified repetitive jobs. The GS schedules the workload to maximize the workload allocated to active servers/racks, assuming VM support on all nodes. This allocation uses the thermal data—obtained from the compact model as well as from thermal sensors and using service guarantees as a constraint. Cooling requirements and changes to the energy budget for the computing/storage and communication equipment for the allocated workload are also assigned based on a variety of heuristics. Some possible heuristics include (but are not limited to):

Extrapolate the thermal output of the active servers and revise its energy budget and cooling requirement based on the updates to number of jobs (existing plus newly-assigned) assigned to the server.

Use the energy requirement characteristics of known, repetitive jobs and the heuristic above for unclassified jobs to plan the schedule.

Use the data maintained on the average job completion rate and average energy requirement of jobs to guide the allocations.

As mentioned earlier, the GS keeps track of the job dispatch rate and the size of the incoming queues in the front-end load balancing switches to keep track of the workload trend. This trend data is used to activate or deactivate servers and racks and redirect cooling efforts as needed. The energy expended in such activation/deactivation and in migrating VMs, where necessary is accounted for in the allocations.

Alternative scheduling may also be employed, including ones that dynamically switch scheduling strategies based on the thermal conditions and current workload. As an example, if all servers are being operated in the high energy-efficiency region as shown in FIG. 2B, then it may be better to perform an allocation that balances the load across the racks to avoid the formation of hot spots in the server room.

The GS has similarities with data center configuration systems and mangers from several vendors (e.g., IBM's Tivoli suite) [IBM 08a, IBM 08b]. However, the present system differs from these schedulers in at least the way server energy dissipation estimates are made at a finer granularity, in making use of a thermal model to predict and cope with thermal conditions, and in using dynamic cooling systems.

Control Systems Issues

The present technique is essentially a control system that employs reactive as well as proactive actuations to meet the goal of improving the overall energy efficiency of a data center. As such, it has to be scalable, stable and provide appropriate sense-and-actuate latencies. Another important requirement of the system is that the various control elements should act in a synchronized and coordinated manner, avoiding "power struggles" [RRT+08], where one control loop fights against another inadvertently.

On the control elements at the computing side, these control system requirements are met by a using a hierarchical implementation that uses independent control elements at each level and by using a progressive top-down approach to dictate the energy/performance goals of one level to be explicitly dictated by the control system at the immediately upper level. The hierarchical control mechanisms of the activities within a computing system also ensures its scalability: separate control loops are used to ensure the energy budgets at the rack level and at the level of individual servers within the rack are monitored and managed separately. For large data centers, another level can be added to make the system more scalable, based on the allocation and control of the energy budgets for a set of neighboring racks.

The control of the computing equipment is based on the notion of update intervals within a sampling period, with sensor and model outputs collected at the end of each update period. At the end of a sampling period, the values of respective sensor and model data output are averaged, and control decisions taken at the end of a sampling period based on these average values, as introduced in [PKG 01]. This approach smoothes out the impact of burst activities that are inevitable within a sampling interval and enables a stable control system for the computing elements.

Hardware Overview

Figure 3:
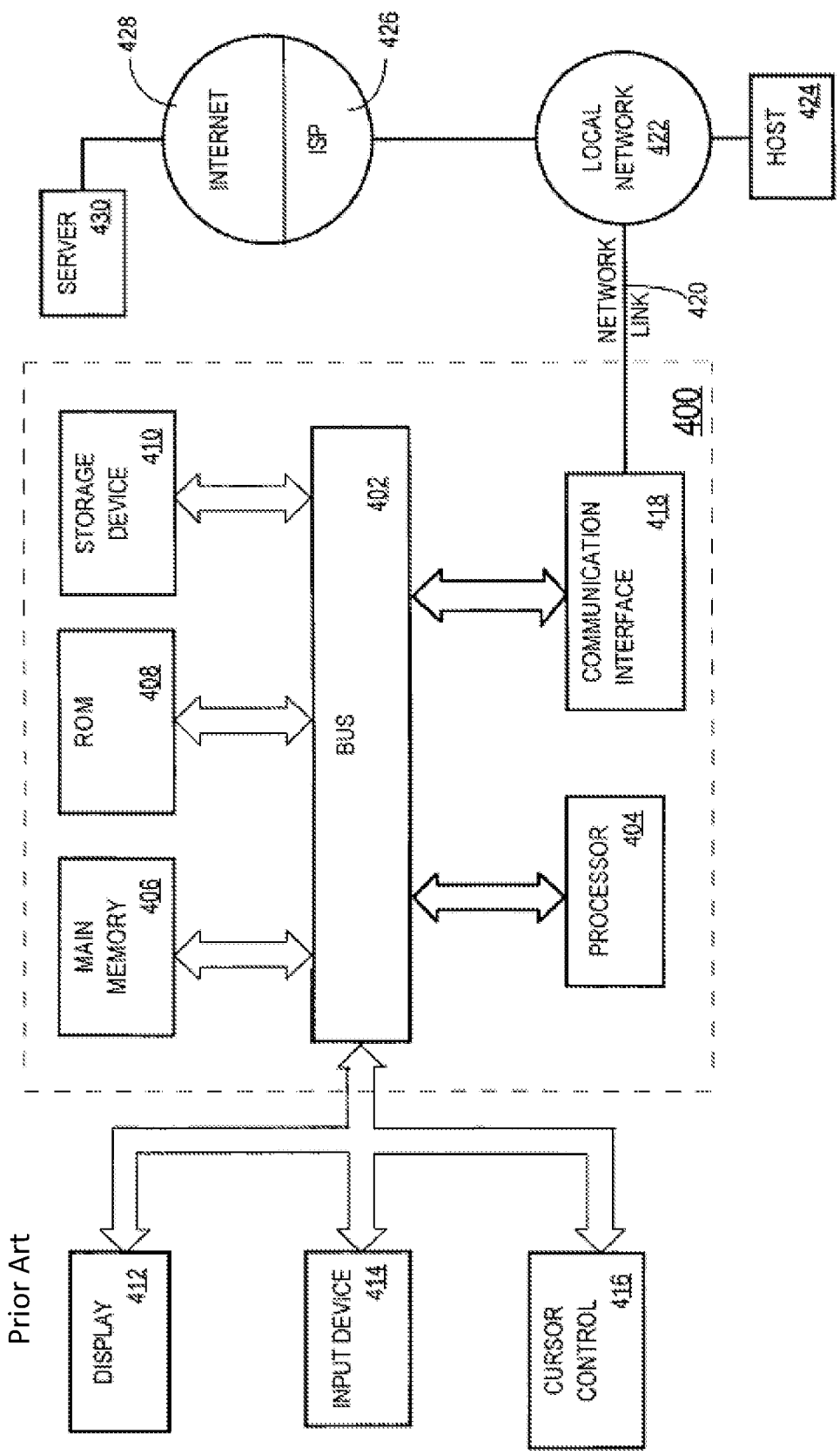
FIG. 3 shows a block diagram of a prior art computing system.

FIG. 3 (see U.S. Pat. No. 7,702,660, issued to Chan, expressly incorporated herein by reference), shows a block diagram that illustrates a computer system 400 upon which an embodiment of the invention may be implemented. Computer system 400 includes a bus 402 or other communication mechanism for communicating information, and a processor 404 coupled with bus 402 for processing information. Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Computer system 400 further includes a read only memory (ROM) 408 or other static storage device coupled to bus 402 for storing static information and instructions for processor 404. A storage device 410, such as a magnetic disk or optical disk, is provided and coupled to bus 402 for storing information and instructions.

Computer system 400 may be coupled via bus 402 to a display 412, such as a cathode ray tube (CRT) or liquid crystal flat panel display, for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

The invention is related to the use of computer system 400 for implementing the techniques described herein. According to one embodiment of the invention, those techniques are performed by computer system 400 in response to processor 404 executing one or more sequences of one or more instructions contained in main memory 406. Such instructions may be read into main memory 406 from another machine-readable medium, such as storage device 410. Execution of the sequences of instructions contained in main memory 406 causes processor 404 to perform the process steps described herein. In alternative embodiments, hard-wired circuitry may be used in place of or in combination with software instructions to implement the invention. Thus, embodiments of the invention are not limited to any specific combination of hardware circuitry and software.

The term "machine-readable medium" as used herein refers to any medium that participates in providing data that causes a machine to operation in a specific fashion. In an embodiment implemented using computer system 400, various machine-readable media are involved, for example, in providing instructions to processor 404 for execution. Such a medium may take many forms, including but not limited to, non-volatile media, volatile media, and transmission media. Non-volatile media includes, for example, optical or magnetic disks, such as storage device 410. Volatile media includes dynamic memory, such as main memory 406. Transmission media includes coaxial cables, copper wire and fiber optics, including the wires that comprise bus 402. Transmission media can also take the form of acoustic or light waves, such as those generated during radio-wave and infra-red data communications. All such media must be tangible to enable the instructions carried by the media to be detected by a physical mechanism that reads the instructions into a machine.

Common forms of machine-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of machine-readable media may be involved in carrying one or more sequences of one or more instructions to processor 404 for execution. For example, the instructions may initially be carried on a magnetic disk of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are exemplary forms of carrier waves transporting the information.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution. In this manner, computer system 400 may obtain application code in the form of a carrier wave.

In this description, several preferred embodiments were discussed. Persons skilled in the art will, undoubtedly, have other ideas as to how the systems and methods described herein may be used. It is understood that this broad invention is not limited to the embodiments discussed herein. Rather, the invention is limited only by the following claims.

REFERENCES (EACH OF WHICH IS
EXPRESSLY INCORPORATED BY
REFERENCE)

U.S. Pat. No. 7,228,441 B2

[BH 07] Luiz André Barroso and Urs Hölzle, "The Case for Energy-Proportional Computing", IEEE Computer Magazine, December 2007.

[BH 09] Luiz André Barroso and Urs Hölzle, "The Datacenter as a Computer: An Introduction to the Design of Warehouse-Scale Machines", Morgan-Claypool Publisshers, 2009 (ISBN No. 9781598295566).

[ERK+08] D. Economou Suzanne Rivoire, Christos Kozyrakis, and Parthasarathy Ranganathan, "Full-system Power Analysis and Modeling for Server Environments", in Proc. Workshop on Modeling Benchmarking and Simulation (MOBS) at the Int'l. Symposium on Computer Architecture, Boston, MA, June 2006.

[IBM 08a] IBM Corporation, *IBM Tivoli Usage Accounting Manager V7.1 Handbook*, IBM Redbook, March 2008.

[IBM 08b] IBM Corporation, *Value Proposition for IBM Systems Director: Challenges of Operational Management for Enterprise Server Installations*, IBM ITG Group, Mangement Brief (34 pages), November 2008.

[Ko 07] Jonathan G. Koomey, "Estimating Total Power Consumption By Servers in the U.S. and the World", Analytics Press. February 2007. Also available at: enterprise.amd.com/us-en/AMD-Business/Technology-Home/Power-Management.aspx.

[LGT 08] Adam Lewis, Soumik Ghosh and N.-F. Tzeng, "Run-time Energy Consumption Estimation Based on Workload in Server Systems", in Proc. of the HotPower 08 workshop, held in conjunction with the 2008 Usenix OSDI Symposium.

[LRC+08] Kevin Lim, Parthasarathy Ranganathan, Jichuan Chang, Chandrakant Patel, Trevor Mudge, Steven Reinhardt, "Understanding and Designing New Server Architectures for Emerging Warehouse-Computing Environments", in Proc. of the 35th International Symposium on Computer Architecture, 2008, pp. 315-326.

[NSSJ 09] Ripal Nathuji, Ankit Somani, Karsten Schwan, and Yogendra Joshi, "CoolIT: Coordinating Facility and IT Management for Efficient Datacenters", in Proc. of the HotPower 08 workshop, held in conjunction with the 2008 Usenix OSDI Symposium.

[PKG 01] Dmitry Ponomarev, Gurhan Kucuk and Kanad Ghose, "Reducing Power Requirements of Instruction Scheduling Through Dynamic Allocation of Multiple Datapath Resources", in Proc. 34th IEEE/ACM International Symposium on Microarchitecture (MICRO-34), December 2001, pp. 90-101.

[RRT+08] Ramya Raghavendra, Parthasarathy Ranganathan, Vanish Talwar, Zhikui Wnag, and Xiaoyun Zhu, "No Power Struggles: Coordinated Multilevel Power Management for the Data Center", in Proc. ACM Symposium on Architectural Support for Programming Languages and Operating Systems (ASPLOS), 2008.

[Sh 09] Stephen Shankland, "Google Uncloaks Once-Secret Server", CNET News, Business Tech, April, 2009, available at: news.cnet.com/8301-1001_3-10209580-92.html.

[SBP+05] Ratnesh K. Sharma, Cullen Bash, Chandrakant D. Patel, Richard J. Friedrich, Jeffrey S. Chase: Balance of Power: Dynamic Thermal Management for Internet Data Centers. IEEE Internet Computing Vol. 9, No. 1, pp. 42-49, 2005.

[TGV 08] Qinghui Tang, Member, Sandeep K. S. Gupta, and Georgios Varsamopoulos, "Energy-Efficient, Thermal-Aware Task Scheduling for Homogeneous, High Performance Computing Data Centers: A Cyber-Physical Approach", in IEEE Trans. On Parallel and Distributed Systems, November 2008 (vol. 19 no. 11) pp. 1458-1472.

What is claimed is:

1. A load distributor for a set of servers, the set of servers being associated with a cooling system, each server having respective energy consumption and performance characteristics, the load distributor comprising:
    an input configured to receive a new task to be processed;
    at least one processor, configured to analyze the new task, and to allocate the new task to a respective server of the set of servers to optimize an energy efficiency of the set of servers, dependent on at least:
        the respective energy consumption and performance characteristics of each server of the set of servers, and
        a thermal environment of each server of the set of servers; and
    an output configured to communicate the allocation of the task to the respective server.

2. The load distributor according to claim 1, further comprising a queue comprising a set of existing tasks pending processing, wherein the at least one processor is further configured to reallocate an existing task for processing by a first server to a second server selectively dependent on a risk of exceeding a thermal constraint by the first server.

3. The load distributor according to claim 1, wherein the cooling system comprises an associated dynamically controllable cooling system for each server, and the at least one automated processor is further configured to alter the associated dynamically controllable cooling system in dependence on a predicted effect of the new task on the thermal environment of the respective server.

4. The load distributor according to claim 3, wherein the at least one automated processor is further configured to control the associated dynamically controllable cooling system for the respective server in anticipation of at least a future workload of the respective server.

5. The load distributor according to claim 1, wherein the at least one automated processor is further configured to activate and deactivate the respective server.

6. The load distributor according to claim 1, wherein the at least one automated processor is further configured to allocate the new task to a respective server selectively in dependence on a predicted efficiency of the cooling system.

7. The load distributor according to claim 1, wherein the at least one automated processor is further configured to allocate the new task to a respective server selectively in dependence on a predicted efficiency of the cooling system.

8. The load distributor according to claim 1, further comprising a thermal and performance computational model of the respective server, wherein the at least one automated processor is further configured to predict a temperature of the respective server based on at least the thermal and performance computational model a sequence of tasks performed by the respective server.

9. The load distributor according to claim 1, wherein the respective server has a dynamic voltage and frequency scaling setting, the set of servers comprise servers having a plurality of different dynamic voltage and frequency scaling settings, and at least one automated processor is further configured to characterize the new task with respect to a repetitive task type, and to allocate the characterized new task to the respective server selectively based on the dynamic voltage and frequency scaling setting.

10. The load distributor according to claim 1, wherein the at least one automated processor is further configured to allocate the task to the respective server further dependent on a headroom of the respective server to accept additional tasks after allocation of the respective task to the respective server.

11. The load distributor according to claim 1, wherein the energy efficiency of the set of servers comprises an energy consumption of a cooling system for the set of servers.

12. The load distributor according to claim 1, wherein the at least one processor is further configured to concentrate allocation of tasks to a subset of an available portion of the set of servers.

13. A load distributor for a set of servers, each server having respective energy consumption and performance characteristics and an associated cooling system, the load distributor comprising:
    an input configured to receive a new task to be processed, the task having a value of execution and an energy consumption of execution;
    at least one processor, configured to analyze the new task, and to allocate the new task to a respective server of the set of servers to optimize a cost-benefit of the set of servers, dependent on at least:
        the respective energy consumption and performance characteristics of each server of the set of servers,
        an energy consumption of the associated cooling system for each server, and
        a thermal environment of each server of the set of servers; and
    an output configured to communicate the allocation of the task to the respective server.

14. The load distributor according to claim 13, further comprising a queue comprising a set of existing tasks pending processing, wherein the at least one processor is further configured to reallocate an existing task for processing by a first server to a second server selectively dependent on a risk of exceeding a thermal constraint by the first server.

15. The load distributor according to claim 13, wherein the at least one automated processor is further configured to dynamically alter the associated cooling system in dependence on a predicted effect of the new task on the thermal environment of the respective server.

16. The load distributor according to claim 13, wherein the at least one automated processor is further configured to control a cooling system for the respective server in anticipation of at least a future workload of the respective server.

17. The load distributor according to claim 13, further comprising a thermal and performance computational model of the respective server, wherein the at least one automated processor is further configured to predict a temperature of the respective server based on at least the thermal and performance computational model a sequence of tasks performed by the respective server.

18. The load distributor according to claim 13, wherein the respective server has a dynamic voltage and frequency scaling setting, the set of servers comprise servers having a plurality of different dynamic voltage and frequency scaling settings, and at least one automated processor is further configured to characterize the new task with respect to a repetitive task type, and to allocate the characterized new task to the respective server selectively based on the dynamic voltage and frequency scaling setting.

19. A method of distributing computational tasks to a set of server systems, the set of server systems being associated with a cooling system, each server system having respective energy consumption and performance characteristics, the method comprising:
- receiving a new task to be processed;
- analyzing the new task;
- allocating the new task to a respective server system of the set of servers to optimize an energy efficiency of the set of server systems, dependent on at least:
  - the respective energy consumption and performance characteristics of each server system of the set of server systems, and
  - a thermal environment of each server system of the set of server systems; and
- communicating the allocation of the task to the respective server system.

20. The method according to claim 19, wherein the energy efficiency of the set of server systems comprises an energy consumption of a computational component configured to process the new task, and an energy consumption of the cooling system.

* * * * *